United States Patent
Anastassov et al.

(10) Patent No.: US 9,844,530 B1
(45) Date of Patent: Dec. 19, 2017

(54) OPHTHALMIC SOLUTIONS FOR GLAUCOMA AND CONJUNCTIVITIS TREATMENT

(71) Applicant: Axim Biotechnologies, Inc., New York, NY (US)

(72) Inventors: George Anastassov, New York, NY (US); Lekhram Changoer, Ridderkerk (NL)

(73) Assignee: Axim Biotechnologies, Inc., New York, NY (US)

( * ) Notice: Subject to any disclaimer, the term of this patent is extended or adjusted under 35 U.S.C. 154(b) by 0 days.

(21) Appl. No.: 15/728,283

(22) Filed: Oct. 9, 2017

Related U.S. Application Data

(62) Division of application No. 14/982,610, filed on Dec. 29, 2015, now Pat. No. 9,814,695.

(60) Provisional application No. 62/098,007, filed on Dec. 30, 2014.

(51) Int. Cl.
| | | |
|---|---|---|
| *A61K 31/05* | (2006.01) | |
| *A61K 31/352* | (2006.01) | |
| *A61K 9/00* | (2006.01) | |
| *A61K 9/08* | (2006.01) | |

(52) U.S. Cl.
CPC .......... *A61K 31/352* (2013.01); *A61K 9/0048* (2013.01); *A61K 31/05* (2013.01); *A61K 9/08* (2013.01)

(58) Field of Classification Search
CPC ............................ A61K 31/05; A61K 31/352
See application file for complete search history.

(56) References Cited

U.S. PATENT DOCUMENTS

| | | | | |
|---|---|---|---|---|
| 6,630,507 | B1* | 10/2003 | Hampson | A61K 31/35 514/454 |
| 8,222,292 | B2* | 7/2012 | Goskonda | A61K 9/0095 514/454 |
| 2007/0249581 | A1* | 10/2007 | Chen | A61K 31/445 514/211.06 |
| 2010/0216872 | A1* | 8/2010 | Letzel | A61K 36/185 514/454 |
| 2010/0273895 | A1* | 10/2010 | Stinchcomb | A61K 9/0014 514/733 |

\* cited by examiner

*Primary Examiner* — Zohreh A Fay
(74) *Attorney, Agent, or Firm* — Premium IP Services, P.C.; Khanh T. Glatzel

(57) ABSTRACT

This invention generally relates to methods of treatment of glaucoma and symptomatic relief of conjunctival inflammation. An ophthalmic solution comprising cannabinoids for the treatment of glaucoma and an ophthalmic solution comprising cannabinoids for these purposes are disclosed. Cannabinoids are selected to achieve the specific purpose of the respective ophthalmic solution.

18 Claims, No Drawings

OPHTHALMIC SOLUTIONS FOR GLAUCOMA AND CONJUNCTIVITIS TREATMENT

CROSS-REFERENCE TO RELATED APPLICATIONS

This application is a divisional of U.S. application Ser. No. 14/982,610, filed Dec. 29, 2015, which claims the benefit of U.S. Provisional Application No. 62/098,007, filed Dec. 30, 2014. Each of the above-referenced patent applications is incorporated by reference in its entirety.

BACKGROUND OF THE INVENTION

Field of the Invention

The present invention generally relates to ophthalmic solutions and uses thereof. The ophthalmic solutions treat glaucoma and conjunctival inflammation in human subjects.

Description of the Related Technology

Glaucoma is one of the leading causes of blindness worldwide. In the U.S. there are approximately 2.5 million sufferers of glaucoma. Glaucoma refers to a group of diseases that damage the eye's optic nerve and can result in vision loss and eventually, blindness. Glaucoma is caused by an increase in the intraocular pressure (TOP), which eventually leads to optic nerve degeneration and blindness.

In the front of the eye is an anterior chamber, wherein a clear fluid flows in and out continuously through a drainage angle at the meeting point of the iris and the cornea. When the drainage angle is affected, fluid does not drain fast enough or does not drain at all, causing a buildup in eye pressure. High pressure may cause damages to optic nerves, which in turn causes vision loss and blindness.

High blood pressure is a contributing factor to glaucoma. However, glaucoma may happen even without pressure buildup in the eye chamber. Glaucoma affects different ethnic groups differently. In the African-American population, glaucoma is the leading cause of blindness. The Hispanic population is also affected by glaucoma more than other ethnic groups.

Age-related macular degeneration (AMD) is a leading cause of vision loss among people age fifty (50) and older. In AMD, the macula, a small spot near the retina in the back of the ocular globe, is damaged. In patients with AMD, a blurred area in the central vision range appears and grows, eventually resulting in a blind spot in the central vision. Treatments for intermediate and acute AMD include vitamin therapy, such as vitamin C, vitamin E, and supplement therapy, such as zinc, cupric oxide, or lutein and zeaxanthin supplements. However, effective treatments for AMD are still sought.

Conjunctivitis is the infection or inflammation of the transparent membrane (conjunctiva) that lines the eyelid and covers the white part of the eyeball. In conjunctivitis, small blood vessels in the conjunctiva are inflamed and appear to be pink or red.

Conjunctivitis is caused by bacterial or viral infection or by allergies. In infants, an incomplete open tear duct may cause conjunctivitis. Early treatment of conjunctivitis prevents spreading, as certain conjunctivitis conditions can be contagious.

The *cannabis* plant has many naturally occurring substances that are of great interest in the fields of science and medicine. Isolated compounds from the *cannabis* plant include $\Delta^9$-tetrahydrocannabinol (THC), cannabidiol (CBD), cannabichromene (CBC), cannabigerol (CBG), cannabidivarin (CBDV), among other compounds. While THC has psychoactive effects, CBD, CBC, CBG, and CBDV do not. Isolated compounds from the *cannabis* plant are called cannabinoids. There are a total of eighty five (85) cannabinoids that have been isolated from the *cannabis* plant. Many researchers have confirmed the medicinal value of cannabinoids. Cannabinoids have been investigated for possible treatment of seizures, nausea, vomiting, lack of appetite, pain, arthritis, inflammation, and other conditions.

The IUPAC nomenclature of THC is (−)-(6aR,10aR)-6,6,9-trimethyl-3-pentyl-6a,7,8,10a-tetrahydro-6H-benzo[c]chromen-1-ol. CBD's IUPAC nomenclature is 2-((1S,6S)-3-methyl-6-(prop-1-en-2-yl)cyclo-hex-2-enyl)-5-pentylbenzene-1,3-diol). CBC has the IUPAC nomenclature of 2-methyl-2-(4-methylpent-3-enyl)-7pentyl-5-chromenol. These are among the most prominent compounds in the family of compounds extracted from the *cannabis* plant referred to as cannabinoids.

Cannabinoids can be isolated by extraction or pressing from *cannabis* plants. Plants in the *cannabis* genus include *Cannabis sativa, Cannabis ruderalis*, and *Cannabis* indica. These plants are the natural sources of cannabinoids. Cannabinoids are also available in synthetic forms. Methods to synthesize cannabinoids in lab settings were discovered and are still currently practiced. Synthetic cannabinoids are more targeted, in that the synthetic compound usually comes isolated without other cannabinoids mixed in.

Nabilone (racemic(6aR,10aR)-1-hydroxy-6,6-dimethyl-3-(2-methyloctan-2-yl)-7,8,10,10a-tetrahydro-6H-benzo[c]chromen-9(6aH)-one), a synthetic cannabinoid, is believed to have fewer undesired side effects than THC. Nabilone mimics the chemical compound structure of THC. THC also exists in synthetic form under the name Dronabinol ((−)-(6aR,10aR)-6,6,9-trimythel-3-pentyl-6a,7,8,10a-tetrahydro-6H-benzo[c]chromen-1-ol)). These synthetic cannabinoids are being investigated for medicinal purposes. The U.S. Food and Drug Administration approved nabilone for treatment of chemotherapy-induced nausea and vomiting. In the United States, nabilone is marketed under the name Cesamet®.

Cannabinoids have neuroprotective properties, especially cannabidiol and cannabigerol. Glaucoma is essentially the damage of optic nerve, and cannabinoids are useful in treating this damage. Moreover, cannabinoids also lower TOP when consumed by pulmonary absorptions, intraoral, and intravenous applications.

In AMD, macular degeneration is the main cause, cannabinoids have neuroprotective properties and may slow down the degeneration of optic nerves. Regeneration of the macula may be promoted with the use of cannabinoids.

Cannabinoids also have anti-inflammatory and anti-angiogenic properties. These properties may be utilized in ophthalmitis, wherein ophthalmic tissues are infected; or conjunctivitis, wherein ophthalmic membrane tissues are infected and/or inflamed.

Cannabigerol has anti-bacterial and anti-inflammatory properties, with fast acting mechanisms. Cannabidiol is also anti-bacterial, with a minimum inhibitory concentration at between 0.5-1 µg/mL for various *Staphylococcus aureus* strains. Tetrahydrocannabinol also has anti-inflammatory and anti-bacterial properties.

Various products containing cannabidiol have been marketed in recent years. Cannabidiol may be consumed by ingestion, by inhalation, or by transdermal delivery. THC, CBD, and CBG have been studied for treatment of various indications, including nausea, lack of appetite, pain, epilepsy, etc.

SUMMARY

The present invention generally relates to an ophthalmic solution comprising cannabinoids, specifically THC, CBD, and CBG at specific proportions, in an aqueous solution for treatment of glaucoma. The present invention also relates to an ophthalmic solution comprising CBD and CBG dissolved in balanced saline solution for symptomatic relief of conjunctival inflammation.

ABBREVIATIONS

AMD: Age-related macular degeneration
CBC: Cannabichromene
CBDV: Cannabidivarin
CBD: Cannabidiol
CBG: Cannabigerol
IOP: Intraocular Pressure
IUPAC: International Union of Pure and Applied Chemistry
THC: Tetrahydrocannabinols

DETAILED DESCRIPTION OF CERTAIN INVENTIVE EMBODIMENTS

This present invention is capable of being embodied in various forms. The description below of several embodiments is made with the understanding that the present disclosure is to be considered as an exemplification of the claimed subject matter, and is not intended to limit the attached claims to the specific embodiments illustrated. The headings used throughout this disclosure are provided for convenience only and are not to be construed to limit the claims in any way. Embodiments illustrated under any heading may be combined with embodiments illustrated under any other heading.

The word "cannabinoid" used in this description, claims, and other conjugations is used to mean any compound that interacts with a cannabinoid receptor and other cannabinoid mimetics, including, but not limited to, certain tetrahydropyran analogs ($\Delta^9$-tetrahydrocannabinol, $\Delta^8$-tetrahydrocannabinol, 6,6,9-trimythel-3-pentyl-6H-dibenzo[b,d]pyran-1-ol,3-(1,1-dimethylheptyl)-6,6a7,8,10,10a-hexahydro-1-1hydroxy-6,6-dimythel-9H-dibezo[b, d]pyran-9-ol, (−)-(3S,4S)-7-hydroxy-delta-6-tetrahydrocannabinol-1,1-dimethylheptyl, (+)-(3S,4S)-7-hydroxy-Δ-6-tetrahydrocannabinol, and $\Delta^8$-tetrahydrocannabinol-11-oic acid); certain piperidine analogs (e.g., (−)-(6S,6aR,9R,10aR)-5,6,6a,7,8,9,10,10a-octahydro-6-methyl-1-3-[(R)-1-methyl-4-phenylbutoxy]-1,9-phenanthridinediol 1-acetate)); certain aminoalkylindole analogs (e.g., (R)-(+)-[2,3-dihydro-5-methyl-3-(4-morpholinylm-ethyl)-pyrrolo[1,2,3,-de]-1,4-benzoxazin-6-yl]-1-naphthelenyl-methanone); certain open pyran-ring analogs (e.g., 2-[3-methyl-6-(1-methylethenyl-2-cyclohexen-1-yl]-5-pentyl-1,3-benzendiol, and 4-(1,1-dimethylheptyl)-2,3'-dihydroxy-6'-α-(3-hydroxypropyl)-1',-2',3',4',5',6'-hexahydrobiphenyl), their salts, solvates, metabolites, and metabolic precursors.

The word "cannabidiol" refers to cannabidiol and cannabidiol derivatives. As used in this application, cannabidiol is obtained from industrial hemp extract with trace amount of THC or from *cannabis* extract using high-CBD *cannabis* cultivars.

The word "cannabigerol" refers to cannabigerol and cannabigerol derivatives. As used in this application, cannabigerol is industrial hemp extract with trace amount of THC or from *cannabis* extract.

In embodiments, the ophthalmic solution comprises a combination of cannabinoids to treat glaucoma. The cannabinoids in these embodiments are THC, CBD, and CBG. All three cannabinoids (THC, CBD, and CBG) are present by dissolution from solid cannabinoids.

Cannabinoids used in these embodiments may be in powder form. Cannabinoids may be isolated and freeze dried from cannabinoid solution extracted from the *Cannabis sativa* L. plant. The resulting powder cannabinoid may be dissolved in a water based solution in the presence of emulsifiers and thickeners.

Cannabinoids as used in these embodiments may be substantially free from impurities. Impurities present in cannabinoid powder may be residues from plant materials. Typical purity of cannabinoid powder in dissolvable form is at between 98.0% and 99.9% by weight. Cannabinoid powder in this high purity form may be in white or off-white color.

THC, CBD, and CBG as used in these embodiments may be present in the eye drop solution in different concentrations. THC may be preferably present in the eye drop solution at 0.1 to 0.5 by weight percent, more preferably at 0.1 to 0.2 by weight percent. CBD may be present in the eye drop solution at 0.1 to 0.5 by weight percent, more preferably at 0.15 to 0.3 by weight percent. CBG may be present in the eye drop solution at 0.05 to 0.5 by weight percent, more preferably at 0.1 to 0.3 by weight percent.

Other ingredients may be added into the eye drop solutions, such as a thickener, a buffer, a pH adjusting agent, an antiseptic agent, or a solubilizer. Known methods to prepare eye drop solutions may be used.

The thickeners in this embodiment may include cyclodextrins, hydroxymethyl cellulose or any other macrocyclic olygosaccharide, hydroxylpropyl methyl cellulose, hydroxylpropyl cellulose, polyvinyl alcohol, carboxyvinyl polymer, polyvinylpyrrolidone, carboxymethyl cellulose, polyacrylic acid, sodium polyacrylate, and sodium alginate. The concentration of the thickener may be 0.1 to 2 by weight percent.

The buffer may include, for example, sodium phosphate, sodium dihydrogen phosphate, sodium dihydrogen phosphate dihydrate, disodium hydrogen phosphate, disodium hydrogen phosphate dodecahydrate, potassium phosphate, potassium dihydrogen phosphate, dipotassium hydrogen phosphate, sodium borate, potassium acetate, sodium acetate, sodium citrate, disodium citrate, sodium carbonate, and sodium hydrogen carbonate. The buffer agent may be present in sufficient quantity to keep the pH level near neutral.

The pH adjusting agent may include, for example, lactic acid, citric acid, phosphoric acid, and acetic acid, to reduce pH level; sodium hydroxide, potassium hydroxide, sodium carbonate, and sodium hydrogen carbonate, to increase pH level.

An antiseptic agent may optionally be incorporated into the eye drop solution to treat conjunctival inflammation, if present, or for antiseptic purposes. The antiseptic agent may include, for example, benzalkonium chloride, benzodecinium bromide, chlorhexidine gluconate, benzethonium chloride, sorbic acid, potassium sorbate, methyl parahydroxybenzoate, ethyl parahydroxy benzoate, and butyl parahydrobenzoate. The antiseptic agent may be present in the eye drop solution at a therapeutically effective amount.

The solubilizer may include, for example, vegetable oils and fats or the like such as polysorbate 80, polyoxyethylene hydrogenated castor oil 60, macrogol 4000, polyvinyl alcohol, tyloxapol, polyoxyethylene, polyoxypropylene glycol, and soybean oil. The solubilizer concentration may be present preferably at 0.5 to 3 by weight percent.

The pH of the eye drop solution in this preferred embodiment is preferably adjusted from 6 to 8. Purified water may be the solvent for the eye drop solution.

In other embodiments, the eye drop solution may comprise cannabinoids, specifically CBD and CBG, to treat conjunctival inflammation. Each of CBD and CBG may be present at 0.05 to 0.5 by weight percent, more preferably at 0.1 to 0.3 by weight percent of the eye drop solution. CBD and CBG may be present at equal weight concentration in the eye drop solution according to these embodiments.

To facilitate dissolution of cannabinoids in the eye drop solution, cannabinoids may be encapsulated in liposomal capsules. Alternatively, cannabinoids may be freeze dried and dissolved in an alcohol solution to promote dissolution. Cannabinoids may also be complexed with β-cyclodextrin to increase dissolution rate in water-based solutions.

The ophthalmic solution according to these embodiments may be used to treat glaucoma in human subjects. The ophthalmic solution may be placed in a dropper container. A human subject may receive between 1 to 5 drops of the ophthalmic solution according to this embodiment in each of his or her eyes and then closes his or her eyes for at least 10 seconds. The human subject may repeat this application twice daily.

Other ingredients may be added into the eye drop solutions, such as a thickener, a buffer, a pH adjusting agent, or a solubilizer. The eye drop solution components may be dissolved in a balanced saline solution (BSS). Known methods to prepare eye drop solutions may be used.

The thickener in this embodiment may include cyclodextrins, hydroxymethyl cellulose or any other macrocyclic olygosaccharide, hydroxylpropyl methyl cellulose, hydroxylpropyl cellulose, polyvinyl alcohol, carboxyvinyl polymer, polyvinylpyrrolidone, carboxymethyl cellulose, polyacrylic acid, sodium polyacrylate, and sodium alginate. The concentration of the thickener may be 0.1 to 2 by weight percent.

The buffer may include, for example, sodium phosphate, sodium dihydrogen phosphate, sodium dihydrogen phosphate dihydrate, disodium hydrogen phosphate, disodium hydrogen phosphate dodecahydrate, potassium phosphate, potassium dihydrogen phosphate, dipotassium hydrogen phosphate, sodium borate, potassium acetate, sodium acetate, sodium citrate, disodium citrate, sodium carbonate, and sodium hydrogen carbonate. The buffer agent may be in sufficient quantity to keep pH level near neutral.

The pH adjusting agent may include, for example, lactic acid, citric acid, phosphoric acid, acetic acid, to reduce pH level; sodium hydroxide, potassium hydroxide, sodium carbonate, and sodium hydrogen carbonate, to increase pH level.

The solubilizer may include, for example, vegetable oils and fats or the like such as polysorbate 80, polyoxyethylene hydrogenated castor oil 60, macrogol 4000, polyvinyl alcohol, tyloxapol, polyoxyethylene, polyoxypropylene glycol, and soybean oil. The solubilizer concentration may be present at 0.5 to 3 by weight percent.

The pH of the eye drop solution in this preferred embodiment may be adjusted to 6 to 8. This eye drop solution may be based on a balanced saline solution.

The ophthalmic solution according to these embodiments may be used to treat conjunctivitis in human subjects. The ophthalmic solution according to this embodiment may be placed in a dropper container. A human subject may receive between 1 to 3 drops of the ophthalmic solution according to this embodiment in each of his or her eyes and then may close his or her eyes for at least 5 seconds. The human subject may repeat this application twice daily.

EXAMPLES

Example 1

| Eye drop solution for glaucoma treatment | | |
|---|---|---|
| Raw material | Percentage (%) | Weight (g) |
| THC | 0.15 | 1.5 |
| CBD | 0.25 | 2.5 |
| CBG | 0.25 | 2.5 |
| Hydroxymethyl cellulose | 0.2 | 2 |
| Benzalkonium chloride | 0.02 | 0.2 |
| Polysorbate 80 | 1 | 10 |
| Water | 98.13 | 981.3 |
| Total | 100 | 1000 |

All ingredients as above, except for water, were weighed and added into a mixing flask. Add 970 ml of purified water into the mixing flask. Place the flask on a heat and stirring plate, stir the mixture while heating to 70° C. to allow dissolution. After returning to room temperature, the solution is made exactly 1000 ml by adding purified water.

Example 2

| Eye drop solution for glaucoma treatment | | |
|---|---|---|
| Raw material | Percentage (%) | Weight (g) |
| THC | 0.15 | 1.5 |
| CBD | 0.25 | 2.5 |
| CBG | 0.25 | 2.5 |
| Hydroxymethyl cellulose | 0.2 | 2 |
| Benzalkonium chloride | 0.02 | 0.2 |
| Polysorbate 80 | 1 | 10 |
| Disodium dihydrogen phosphate dodecahydrate | 0.1 | 1 |
| Water | 98.03 | 980.3 |
| Total | 100 | 1000 |

An eye drop solution for glaucoma treatment is prepared as in Example 1, but with 1 g of disodium dihydrogen phosphate dodecahydrate added to stabilize the pH. Water added in the last step is adjusted accordingly to yield 1000 ml of eye drop solution.

Example 3

| Eye drop solution for conjunctival inflammation treatment | | |
|---|---|---|
| Raw material | Percentage (%) | Weight (g) |
| CBD | 0.25 | 2.5 |
| CBG | 0.25 | 2.5 |

-continued

Eye drop solution for conjunctival inflammation treatment

| Raw material | Percentage (%) | Weight (g) |
| --- | --- | --- |
| Hydroxymethyl cellulose | 0.2 | 2 |
| Polysorbate 80 | 1 | 10 |
| Balanced saline solution | 98.3 | 983 |
| Total | 100 | 1000 |

All ingredients as above, except for water, were weighed and added into a mixing flask. Add 970 ml of balanced saline solution into the mixing flask. Place the flask on a heat and stirring plate, stir the mixture while heating to 70° C. to allow dissolution. After returning to room temperature, the solution is made exactly 1000 ml by adding purified water.

All references, including publications, patent applications, and patents cited herein are hereby incorporated by reference to the same extent as if each reference were individually and specifically indicated to be incorporated by reference and were set forth in its entirety herein.

It will be readily apparent to those skilled in the art that a number of modifications and changes may be made without departing from the spirit and the scope of the present invention. It is to be understood that any ranges, ratios, and range of ratios that can be derived from any of the data disclosed herein represent further embodiments of the present disclosure and are included as part of the disclosure as though they were explicitly set forth. This includes ranges that can be formed that do or do not include a finite upper and/or lower boundary. Accordingly, a person of ordinary skill in the art will appreciate that such values are unambiguously derivative from the data presented herein.

What is claimed is:

1. A method to treat glaucoma in a human subject in need thereof, comprising the steps of:
   (a) placing between 1 to 5 drops of an ophthalmic solution in each of the eyes of a human subject having glaucoma, the ophthalmic solution comprising:
      $\Delta^9$-tetrahydrocannabinols at 0.1 to 0.5 weight percent, cannabidiol at 0.1 to 0.5 weight percent, and cannabigerol at 0.05 to 0.5 weight percent;
      a thickener selected from the group consisting of cyclodextrins, hydroxymethyl cellulose, hydroxylpropyl methyl cellulose, hydroxylpropyl cellulose, polyvinyl alcohol, carboxyvinyl polymer, polyvinylpyrrolidone, carboxymethyl cellulose, polyacrylic acid, sodium polyacrylate, and sodium alginate;
      a solubilizer selected from the group consisting of polysorbate 80, polyoxyethylene hydrogenated castor oil 60, macrogol 4000, polyvinyl alcohol, tyloxapol, polyoxyethylene, polyoxypropylene glycol, and soybean oil;
      a buffer selected from the group consisting of sodium phosphate, sodium dihydrogen phosphate, sodium dihydrogen phosphate dihydrate, disodium hydrogen phosphate, disodium hydrogen phosphate dodecahydrate, potassium phosphate, potassium dihydrogen phosphate, dipotassium hydrogen phosphate, sodium borate, potassium acetate, sodium acetate, sodium citrate, disodium citrate, sodium carbonate, and sodium hydrogen carbonate; and
      water;
   (b) the human subject closing his or her eyelids for at least 10 seconds; and
   (c) repeating the application twice daily.

2. The method of claim 1, wherein the ophthalmic solution comprises:
   (a) $\Delta^9$-tetrahydrocannabinols is present in the ophthalmic solution at 0.1 to 0.2 weight percent;
   (b) cannabidiol is present in the ophthalmic solution at 0.15 to 0.3 weight percent; and
   (c) cannabigerol is present in ophthalmic solution at 0.1 to 0.3 weight percent.

3. The method of claim 1, wherein $\Delta^9$-tetrahydrocannabinols, cannabidiol, and cannabigerol are encapsulated in liposomal capsules.

4. The method of claim 1, wherein $\Delta^9$-tetrahydrocannabinols, cannabidiol, and cannabigerol are complexed with β-cyclodextrin.

5. The method of claim 1, wherein the thickener in the ophthalmic solution is present at 0.1 to 2 weight percent.

6. The method of claim 1, wherein the solubilizer in the ophthalmic solution is present at 0.5 to 3 weight percent.

7. The method of claim 1, wherein the ophthalmic solution further comprises an antiseptic agent.

8. The method of claim 7, wherein the antiseptic agent is selected from the group consisting of benzalkonium chloride, benzodecinium bromide, chlorhexidine gluconate, benzethonium chloride, sorbic acid, potassium sorbate, methyl parahydroxybenzoate, ethyl parahydroxybenzoate, and butyl parahydrobenzoate.

9. The method of claim 7, wherein the ophthalmic solution further comprises a pH adjusting agent.

10. The method of claim 9, wherein the pH adjusting agent is selected from the group consisting of lactic acid, citric acid, phosphoric acid, acetic acid, sodium hydroxide, potassium hydroxide, sodium carbonate, and sodium hydrogen carbonate.

11. A method to treat conjunctivitis in a human subject in need thereof comprising the steps of:
   (a) applying between 1 to 3 drops of an ophthalmic solution in the eye of a human subject presenting with conjunctivitis, the ophthalmic solution comprising:
      cannabidiol at 0.05 to 0.5 weight percent and cannabigerol at 0.05 to 0.5 weight percent;
      a thickener selected from the group consisting of cyclodextrins, hydroxymethyl cellulose or any other macrocyclic olygosaccharide, hydroxylpropyl methyl cellulose, hydroxylpropyl cellulose, polyvinyl alcohol, carboxyvinyl polymer, polyvinylpyrrolidone, carboxymethyl cellulose, polyacrylic acid, sodium polyacrylate, and sodium alginate;
      a solubilizer selected from the group consisting of polysorbate 80, polyoxyethylene hydrogenated castor oil 60, macrogol 4000, polyvinyl alcohol, tyloxapol, polyoxyethylene, polyoxypropylene glycol, and soybean oil;
      a buffer selected from the group consisting of sodium phosphate, sodium dihydrogen phosphate, sodium dihydrogen phosphate dihydrate, disodium hydrogen phosphate, disodium hydrogen phosphate dodecahydrate, potassium phosphate, potassium dihydrogen phosphate, dipotassium hydrogen phosphate, sodium borate, potassium acetate, sodium acetate, sodium citrate, disodium citrate, sodium carbonate, and sodium hydrogen carbonate; and
      a balanced saline solution;
   (b) the human subject closing his or her eyelids for at least 5 seconds; and
   (c) repeating the application twice daily.

12. The method of claim 11, wherein:
(a) cannabidiol in the ophthalmic solution is present at 0.1 to 0.3 weight percent; and
(b) cannabigerol in the ophthalmic solution is present at 0.1 to 0.3 weight percent.

13. The method of claim 11, wherein cannabidiol and cannabigerol are encapsulated in liposomal capsules.

14. The method of claim 11, wherein cannabidiol and cannabigerol are complexed with β-cyclodextrin.

15. The method of claim 11, wherein the thickener in the ophthalmic solution is present at 0.1 to 2 weight percent.

16. The method of claim 11, wherein the solubilizer in the ophthalmic solution is present at 0.5 to 3 weight percent.

17. The method of claim 11, wherein the ophthalmic solution further comprises a pH adjusting agent.

18. The method of claim 17, wherein the pH adjusting agent is selected from the group consisting of lactic acid, citric acid, phosphoric acid, acetic acid, sodium hydroxide, potassium hydroxide, sodium carbonate, and sodium hydrogen carbonate.

\* \* \* \* \*